(12) United States Patent
Fritz-Langhals

(10) Patent No.: US 10,329,313 B2
(45) Date of Patent: Jun. 25, 2019

(54) ORGANOSILICON COMPOUNDS HAVING (METH)ACRYLATE GROUPS AND A PROCESS FOR PREPARATION THEREOF

(71) Applicant: Wacker Chemie AG, Munich (DE)

(72) Inventor: Elke Fritz-Langhals, Ottobrunn (DE)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 15/742,457

(22) PCT Filed: Aug. 9, 2016

(86) PCT No.: PCT/EP2016/068945
§ 371 (c)(1),
(2) Date: Jan. 5, 2018

(87) PCT Pub. No.: WO2017/036743
PCT Pub. Date: Mar. 9, 2017

(65) Prior Publication Data
US 2018/0201633 A1    Jul. 19, 2018

(30) Foreign Application Priority Data
Sep. 4, 2015   (DE) .................. 10 2015 216 951

(51) Int. Cl.
*C07F 7/12* (2006.01)
*C07F 7/18* (2006.01)
*C08G 77/00* (2006.01)

(52) U.S. Cl.
CPC .............. *C07F 7/1804* (2013.01); *C07F 7/12* (2013.01); *C07F 7/123* (2013.01); *C08G 77/00* (2013.01)

(58) Field of Classification Search
None
See application file for complete search history.

(56) References Cited

U.S. PATENT DOCUMENTS

| | | |
|---|---|---|
| 4,301,268 A | 11/1981 | Kropac |
| 4,306,050 A | 12/1981 | Koerner et al. |
| 4,963,438 A | 10/1990 | Weitemeyer et al. |
| 4,978,726 A | 12/1990 | Dohler et al. |
| 2005/0136269 A1 | 6/2005 | Doehler et al. |
| 2005/0287300 A1 | 12/2005 | Herrwerth et al. |
| 2012/0245248 A1* | 9/2012 | Alli .................. C08F 290/068 523/107 |

FOREIGN PATENT DOCUMENTS

| | | |
|---|---|---|
| DE | 10359764 A1 | 7/2005 |
| EP | 1544232 A1 | 6/2005 |
| EP | 1595909 A1 | 11/2005 |
| JP | 10245247 A | 9/1998 |
| WO | 2013096587 A1 | 6/2013 |

OTHER PUBLICATIONS

Prasad et al.: "Enantioselective total Synthesis of Iso-Cladospolide B, Cladospolide C and Cladospolide B from Tartaric Acid" Tetrahedron: Asymmetry, 22 (5), 2011, pp. 499-505.

* cited by examiner

*Primary Examiner* — Rosalynd A Keys
*Assistant Examiner* — Kofi Adzamli
(74) *Attorney, Agent, or Firm* — Brooks Kushman P.C.

(57) ABSTRACT

(Meth)acrylate-functionalized silicon compounds are easily prepared by the reaction of a (meth)acryloyl-functionalized chlorosilane with an organosilicon compound having silicon-bonded hydroxy groups. The carbon atom adjacent to the resulting O—Si linkage is bonded to at least one further carbon, rendering the product stable to hydrolysis despite the C—O—Si linkage.

11 Claims, No Drawings

ORGANOSILICON COMPOUNDS HAVING (METH)ACRYLATE GROUPS AND A PROCESS FOR PREPARATION THEREOF

CROSS REFERENCE TO RELATED APPLICATIONS

This application is the U.S. National Phase of PCT Appln. No. PCT/EP2016/068945 filed Aug. 9, 2016, which claims priority to German Application No. 10 2015 216 951.0 filed Sep. 4, 2015, the disclosures of which are incorporated in their entirety by reference herein.

BACKGROUND OF THE INVENTION

1. Field of the Invention

The invention relates to organosilicon compounds bearing (meth)acrylate groups, to a simple process for preparation thereof via (meth)acrylate-functionalized chlorosilanes, and to the (meth)acrylate-functionalized chlorosilanes.

2. Description of the Related Art

Organosilicon compounds bearing (meth)acrylate groups play an important part in large areas of industrial technology. Silicone materials are curable via (meth)acrylate groups for example. Silicone materials are needed inter alia for producing adhesive coatings by radiative curing. The (meth)acrylate group is additionally copolymerizable with further (meth)acrylates in any desired manner to thus obtain novel materials having custom-tailored properties. Long-term stability plays an important part with all these materials.

(Meth)acrylate-functional organosilicon compounds are already known. The general rule with these is that the (meth)acrylate grouping is attached to a siloxane scaffold via a carbon spacer. This Si—C link is invariably brought about via a noble metal-catalyzed addition reaction of organosilicon compounds bearing Si—H groups onto olefins, in a so-called hydrosilylation reaction. The production of the (meth)acrylate grouping has to await a subsequent, further step, or there will be unwanted secondary reactions involving the (meth)acrylate double bond. The Si—C-linked (meth)acrylate-functional organosilicon compounds are obtainable for example as described in U.S. Pat. No. 4,978,726 by first reacting the organosilicon compounds comprising Si—H groups with an olefinic epoxide, for example allyl glycidyl ether, and then attaching the (meth)acrylate grouping by epoxide ring opening.

A further process described in U.S. Pat. No. 4,963,438 consists in first adding the Si—H grouping onto an olefinic alcohol, for example allyl alcohol, and then attaching the (meth)acrylate grouping by esterification with the hydroxyl group.

One disadvantage with these processes is that they each include a noble metal-catalyzed and hence costly reacting step, the hydrosilylation reaction. Another disadvantage with these processes is that the attachment of the (meth)acrylate grouping has to take place in a subsequent polymer-analogous step. In addition, the reactions with acrylic acid in particular are afflicted with the formation of by-products which, if at all, can only be removed from the polymer at very high cost and inconvenience.

U.S. Pat. Nos. 4,301,268 and 4,306,050 for example also disclose Si—O—C-linked (meth)acrylate-functional polysiloxanes, which are prepared by reaction of chloropolysiloxanes with (meth)acrylate-functional alcohols. However, chloropolysiloxanes are not available as large-scale industrial products, since their stability in storage is but limited.

As described in DE 10359764, however, these compounds are insufficiently stable to hydrolysis. Yet the long-term hydrolytic stability of the linker grouping is an important prerequisite for the long-term stability of the products and hence for their industrial utility.

Prior art Si—O—C-linked (meth)acrylate-functional organosilicon compounds are hydrolytically labile in particular when they contain salts, particularly in the form of chlorides, from their synthesis.

This problem is solved in DE 10359764 and in EP 1595909 by a synthesis reaction of H-siloxanes with acrylate-functional alcohols in the presence of a Lewis acid catalyst. However, this approach is disadvantageous because comparatively costly H-siloxanes have to be used and also because hydrogen is formed in the reaction, necessitating burdensome safety measures. The preferred Lewis acids are very costly perfluorinated organoboron compounds which, owing to their low volatility, are impossible to remove from the polymer, and thus remain in the end products, thereby constituting an environmental problem.

There is accordingly a need for (meth)acrylate-functional organosilicon compounds that are obtainable in a simple and cost-effective manner. Compounds are of particular interest which are obtainable without a hydrosilylation reaction and without using costly catalysts. A further important requirement for industrial use is that the (meth)acrylate-functional organosilicon compounds be hydrolytically stable even in the presence of impurities.

SUMMARY OF THE INVENTION

The invention provides (meth)acrylate-functional organosilicon compounds M in which an oxygen atom connects the (meth)acrylate group to the silicon of the organosilicon compound, wherein the carbon atom bonded to the oxygen atom bears at least one further moiety bonded via carbon, with the proviso that in the presence of just one further moiety, said moiety contains more than one carbon atom. It has been surprisingly discovered that these (meth)acrylate-functional organosilicon compounds M are hydrolytically stable even in the presence of impurities.

DETAILED DESCRIPTION OF THE PREFERRED EMBODIMENTS

The expression "(meth)acrylate" is to be understood as meaning methacrylate, acrylate or a mixture of methacrylate and acrylate.

Preferably, the (meth)acrylate-functional organosilicon compounds M are constructed of at least one unit of general formula I and no or at least one unit of general formula II

$$R^2_b X_c SiO_{[4-(b+c)]/2} \quad (I),$$

$$R^1_a SiO_{(4-a)/2} \quad (II),$$

where $R^1$ and $R^2$ are each independently hydrogen atoms or $C_1$-$C_{20}$ hydrocarbon or $C_1$-$C_{15}$ hydrocarbonoxy moieties in which one or more mutually nonadjacent methylene units may each be replaced by —O—, —CO—, —COO—, —OCO— or —OCOO or $NR^x$ groups and which are unsubstituted, or substituted with substituents selected from —CN, $NR^x_2$, COOH, $COOR^x$, -halogen, -acryloyl, -methacryloyl, -epoxy, —OH and —$CONR^x_2$, $R^x$ is hydrogen or a $C_1$-$C_{10}$ hydrocarbon moiety, unsubstituted or substituted with substituents selected from —CN and halogen, X is an oxygen-bonded moiety of general formula (III)

$$O—C(R^3R^4)—R^5—O—(C=O)—CR^6=CH_2) \quad (III)$$

$R^3$ and $R^4$ are each independently hydrogen or $C_1$-$C_{20}$ hydrocarbon moieties in which one or more mutually nonadjacent methylene units may each be replaced by O—(C=O)—$CR^6$=$CH_2$, —O—, —CO—, —COO—, —OCO— or —OCOO— or $NR^x$ groups, with the proviso that when $R^3$ is hydrogen, $R^4$ contains at least two carbon atoms, $R^5$ is a divalent $C_1$-$C_{20}$ hydrocarbon moiety in which one or more mutually nonadjacent methylene units may each be replaced by —O—, —CO—, —COO—, —OCO— or —OCOO— or $NR^x$ groups, $R^6$ is hydrogen or unbranched, branched or cyclic saturated or unsaturated alkyl of 1 to 12 carbon atoms or aryl or aralkyl, wherein individual nonadjacent methylene units may be replaced by nitrogen atoms or oxygen atoms, a is 0, 1, 2 or 3,
b is 0, 1 or 2,
c is 1, 2 or 3, and
b+c is 1, 2, 3 or 4.

$R^1$ and $R^2$ preferably have, in the scaffold, from 1 to 12 atoms, especially 1 to 6 atoms, preferably carbon atoms only or one alkoxy oxygen atom and otherwise carbon atoms only as well as hydrogen atoms. $R^1$ and $R^2$ are each preferably straight-chain, branched or cyclic $C_1$-$C_6$ alkyl or alkoxy moieties. The moieties methyl, ethyl, phenyl, vinyl, trifluoropropyl, methoxy, ethoxy and i-propoxy are particularly preferable. The moieties $R^1$ and $R^2$ may be the same or different and attached to the same silicon atom.

$R^3$ and $R^4$ preferably have 1 to 12 carbon atoms, especially 1 to 6 carbon atoms, preferably just carbon atoms or oxygen atoms or just carbon atoms in addition to hydrogen. When $R^3$ is a hydrogen atom, $R^4$ must contain at least two carbon atoms. $R^3$ and $R^4$ are preferably straight-chain, branched or cyclic $C_1$-$C_6$ alkyl moieties or aryl moieties which may contain one or more further (meth)acrylate groupings. The moieties methyl, ethyl and (meth)acryloyloxymethyl are particularly preferable.

It is particularly preferable for the $R^3$ and $R^4$ moieties to both be methyl.

The $R^5$ moiety is preferably a divalent C-bonded $C_1$-$C_6$ hydrocarbon moiety wherein nonadjacent methylene groups may be replaced by oxygens. $R^5$ is preferably a straight-chain or branched alkylene moiety. The alkylene moieties methylene, ethylene, propylene or butylene are particularly preferable.

$R^6$ is preferably hydrogen or unbranched, branched or cyclic saturated or unsaturated alkyl of 1 to 6 carbon atoms or aryl.

$R^6$ is more preferably hydrogen or $C_1$-$C_5$ alkyl.
$R^6$ is most preferably hydrogen.
c is preferably 1.

The (meth)acrylate-functional organosilicon compounds M may be linear, branched, cyclic, bicyclic, tricyclic or polycyclic. They may be oils, resins or particles.

The (meth)acrylate-functional organosilicon compounds M preferably contain 1 to 20, especially 2 to 10 units of general formula I. The (meth)acrylate-functional organosilicon compounds preferably contain 1 to 500, more preferably 4 to 200, especially 10 to 100 units of general formula II.

It is preferable for a to be 2 in at least 90%, especially at least 95% of units of general formula II.

Examples of groupings X are:
O—C(CH_3)_2—CH_2—O—(C=O)—CH=CH_2,
O—C(CH_3)_2—CH(CH_3)—O—(C=O)—CH=CH_2,
O—C(CH_3)_2—CH_2—CH_2—O—(C=O)—CH=CH_2,
O—C(CH_3)_2—CH_2—CH(CH_3)—O—(C=O)—CH=CH_2,
O—CH(C_2H_5)—CH_2—O—(C=O)—CH=CH_2, and
O—CH [CH_2—O—(C=O)—CH=CH_2]_2.

The invention further provides a process for preparing (meth)acrylate-functionalized organosilicon compounds M constructed of at least one unit of general formula I and no or at least one unit of general formula II $$R^2{}_bX_cSiO_{[4-(b+c)]/2} \quad (I),$$

$$R^1{}_aSiO_{(4-a)/2} \quad (II),$$

which process comprises reacting (meth)acryloyl-functionalized chlorosilanes of general formula IV $$R^2{}_bX_cSiCl_{[4-(b+c)]} \quad (IV)$$

with hydroxyl-functionalized organosilicon compounds, wherein $R^1$, $R^2$, X, a, b and c each have the above meanings and preferred meanings.

The invention further provides a process for preparing the (meth)acrylate-functionalized chlorosilanes of general formula IV $$R^2{}_bX_cSiCl_{[4-(b+c)]} \quad (IV),$$

which process comprises reacting (meth)acryloyl-functionalized alcohols of general formula V $$HO—C(R^3R^4)—R^5—O—(C=O)—CR^6=CH_2 \quad (V)$$

with chlorosilanes of general formula VI $$R^2{}_bSiCl_{[4-b]} \quad (VI)$$

wherein $R^2$, $R^3$, $R^4$, $R^5$, $R^6$, X, b and c each have the above meanings and preferred meanings.

The invention further also provides (meth)acryloyl-functionalized chlorosilanes of general formula IV $$R^2{}_bX_cSiCl_{[4-(b+c)]} \quad (IV)$$

where $R^2$, X, b and c each have the above meanings and preferred meanings.

The (meth)acryloyl-functionalized chlorosilanes of general formula IV are thus useful for preparing the (meth)acrylate-functionalized organosilicon compounds M out of organosilicon compounds available on a large industrial scale, such as hydroxypolysiloxanes or hydroxypolysiloxanes in admixture with siloxane cycles.

Hitherto there was no industrially suitable simple way to prepare the (meth)acrylate-functionalized organosilicon compounds M.

EP 1544232 describes the preparation of (meth)acrylate-functionalized polysiloxanes linked to the silicon via an oxygen atom by dehydrogenative linking between a hydride-functional siloxane and a hydroxyl-functional acrylate by use of Lewis acids, especially perfluorinated organoboron compounds as catalysts. This method of synthesis utilizes a very costly catalyst that cannot be removed from the product. Moreover, the formation of hydrogen in the reaction also poses high safety challenges.

U.S. Pat. Nos. 4,301,268 and 4,306,050 also describe the preparation of Si—O—C-linked (meth)acrylate-functional polysiloxanes, which are prepared by reaction of chloropolysiloxanes with (meth)acrylate-functional alcohols. However, chloropolysiloxanes are not available as large-scale industrial products, since their stability in storage is but limited.

There is accordingly also a need for a simple and cost-effective process for preparation of (meth)acrylate-functional Si—O—C-linked organosilicon compounds. It would be particularly advantageous to have a process capable of employing organosilicon compounds available in a stable form on a large industrial scale, examples being hydroxypolysiloxanes or hydroxypolysiloxanes in admixture with siloxane cycles.

It was found that, surprisingly, the (meth)acrylate-functional Si—O—C-linked organosilicon compounds M are easy to prepare from (meth)acryloyloxy-functionalized chlorosilanes. These in turn are very easily obtainable from the (meth)acryloyloxy-functional alcohols and alkylchlorosilanes.

The (meth)acrylate-functional alcohols of general formula V which are used are obtainable in a manner known to a skilled person, for example by esterification of di- or polyols and (meth)acryloyl chloride in the presence of a base, for example triethylamine, or by azeotropic esterification of diols with (meth)acrylic acid. In the presence of two or more chemically identical hydroxyl groups, the degree of conversion is controllable through the amount of (meth)acrylic acid or (meth)acryloyl chloride relative to the number of hydroxyl groups present. In the case di- or polyols having chemically different hydroxyl groups, the esterification is generally effected in a regioselective preferential manner on the sterically less hindered position, i.e., for example on a primary or secondary alcohol grouping in preference to a tertiary alcohol grouping.

Examples of alcohols used with preference to prepare the (meth)acryloyl-functionalized alcohols of general formula V include 2-methyl-1,2-propanediol, 2-methyl-2,3-butanediol, 3-methyl-1,3-butanediol, 2-methyl-2,4-pentanediol, 1,2-butanediol and glycerol.

A further possible method to prepare the (meth)acrylate-functional alcohols V is the ring opening of epoxides with (meth)acrylic acid or salts thereof, for example the reaction of 2,2-dimethylethylene oxide with acrylic acid that is described in WO 2013096587.

The reaction of the (meth)acrylate-functional alcohols of general formula V with chlorosilanes of general formula VI to afford the (meth)acrylate-functional chlorosilanes of general formula IV may be carried out as a batch reaction, as a semi-batch reaction or in a continuous manner.

In the preferred procedure, the chlorosilane of general formula VI is initially charged, optionally in an inert solvent, and the (meth)acrylate-functional alcohol of general formula V, optionally likewise in an inert solvent, is metered in. Useful inert solvents include, for example, toluene, methyl tert-butyl ether, dichloromethane, cyclohexane or mixtures thereof. The proportion of inert solvent is preferably at least 5 wt % and at most 1000 wt %, more preferably at least 20 wt % and at most 300 wt % and more preferably at least 50 wt % and at most 200 wt %, based on the reaction mass of the chlorosilane of general formula VI and the (meth)acrylate-functional alcohol of general formula V, without solvent.

The (meth)acrylate-functional alcohol of general formula V is preferably used in molar deficiency based on all chlorine groupings present in the chlorosilane of general formula VI, so there will be at least one Si—Cl unit following the reaction. For example, with tetrachlorosilane it is preferably at least 0.8 and at most 3.3 equivalents and more preferably at least 1.0 and at most 2.2 equivalents which are used of (meth)acrylate-functional alcohol of general formula V which are use; with trichlorosilanes it is preferably at least 0.8 and at most 2.2 equivalents and more preferably at least 1.0 and at most 1.2 equivalents; with dichlorosilanes it is preferably at least 0.8 and at most 1.3 equivalents, and more preferably at least 0.9 and at most 1.2 equivalents.

The reaction for binding the hydrogen chloride formed preferably takes place in the presence of a base, more preferably in the presence of ammonia or of an organic type amine base, for example triethylamine or tributylamine.

The base is preferably added to the (meth)acrylate-functional alcohol of general formula V. It is further possible to meter in the base separately.

The base is preferably used in proportions of at least 0.8 equivalent and at most 1.3 equivalents, more preferably in proportions of at least 0.9 equivalent and at most 1.2 equivalents, based on the alcohol grouping of the deployed (meth)acrylate-functional alcohol of general formula V.

The reaction time is preferably at least 1 min and at most 50 hours, more preferably at least 30 min and at most 20 hours, yet more preferably at least 1 hour and at most 10 hours.

The reaction is preferably carried out temperatures between 0 and 180° C., more preferably between 20 and 120° C., and at pressures preferably between 100 mbar and 10 bar, more preferably between 1 and 5 bar.

The resultant (meth)acrylate-functional chlorosilanes of general formula IV are reacted with hydroxy-functional siloxanes to afford the (meth)acrylate-functional polysiloxanes M.

This reaction may be carried out as a batch reaction, as a semi-batch reaction or in a continuous manner.

In a preferred procedure, the hydroxyl-functional siloxane is initially charged, optionally in dilute form, and the (meth)acrylate-functional chlorosilane IV, optionally likewise in dilute form, is metered in.

Useful diluents include, for example, inert solvents such as toluene, methyl tert-butyl ether, dichloromethane, cyclohexane or mixtures thereof. The proportion of inert solvent is preferably at least 5 wt % and at most 1000 wt %, more preferably at least 20 wt % and at most 300 wt % and yet more preferably at least 50 wt % and at most 200 wt %, based on the hydroxypolysiloxane used.

The (meth)acrylate-functional chlorosilane of general formula IV is preferably used in molar proportions of at least 0.2 equivalent and at most 3.0 equivalents, preferably 0.8 equivalent and at most 2 equivalents and more preferably at least 1.0 equivalent and at most 1.3 equivalents, based on the hydroxyl groups present in the hydroxypolysiloxane.

The reaction for binding the hydrogen chloride formed is preferably carried out in the presence of a base, more preferably in the presence of ammonia, of an organic type amine base, or an alkali metal, earth metal or alkaline-earth metal carbonate, bicarbonate or hydroxide. Examples of bases used include potassium carbonate, sodium carbonate and calcium carbonate, sodium hydroxide, potassium hydroxide, ammonia, triethylamine or tributylamine.

The base is preferably added to the hydroxypolysiloxane. It is further possible to meter in the base separately. The base is preferably used in proportions of at least 0.8 equivalent and at most 1.3 equivalents and more preferably in proportions of at least 0.9 equivalent and at most 1.2 equivalents, based on the chlorosilane groupings present.

The reaction time is preferably at least 10 min and at most 200 hours, more preferably at least 1 hour and at most 100 hours and yet more preferably at least 1 hour and at most 70 hours.

In a special embodiment, preferred for (meth)acrylate-functional monochlorosilanes of general formula IV where b+c=3, these are converted with water into the corresponding disiloxanes of general formula I where b+c=3:

$$2R^2{}_bX_cSiCl+H_2O \Rightarrow R^2{}_bX_cSi-O-SiXR^2{}_b+2HCl$$

which are then reacted with terminally hydroxyl-functionalized organosilicon compounds or siloxane cycles or mixtures thereof in an equilibration reaction to afford the corresponding (meth)acrylate-functional polysiloxanes M.

This reaction with water is preferably carried out in the presence of a base, preferably in the presence of an alkali or alkaline-earth metal bicarbonate, carbonate or hydroxide, or in the presence of ammonia, to neutralize the hydrochloric acid formed.

The chlorosilane is preferably reacted with at least 0.5 equivalent of water and at most 100 equivalents of water, more preferably with at least 1 equivalent of water and at most 30 equivalents of water at temperatures between at least 0 and at most 180° C., more preferably between at least 20 and at most 120° C., and pressures preferably between at least 10 mbar and at most 10 bar, more preferably between at least 100 mbar and at most 2 bar.

The disiloxane obtained may be used without further purification before the further reaction with hydroxyl-functional polysiloxane or else may also be purified. For purification, excess water is removed from the crude product, optionally by distilling or extracting the product with an inert solvent, salts formed are optionally separated off, optionally by extraction with water, by filtration or by distillation of the solvent.

The reaction with the hydroxyl-functional polysiloxane or with siloxane cycles, a so-called equilibration reaction, can be carried out in a manner known to one skilled in the art.

All the above symbols in the above formulae each have their meanings independently of each other. The silicon atom is tetravalent in all formulae.

In the examples which follow, unless otherwise stated in particular instance, all amounts and percentages are by weight, all pressures are equal to 0.10 MPa (abs.) and all temperatures are equal to 20° C.

Example 1 (not in Accordance with the Present Invention)

Synthesis of the 2-hydroxy-2-methylpropyl Acrylate Precursor

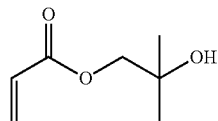

Under inert gas, triethylamine (66.8 g, 91.5 mL, 0.66 mol, 1.2 eq.) and 2-methylpropane-1,2-diol (49.6 g, 0.55 mol, 1 eq.) are initially charged in 300 mL of dichloromethane and cooled to 0° C. with an ice bath. A solution of 200 mL of dichloromethane and acryloyl chloride (49.8 g, 44.5 mL, 0.55 mol, 1 eq.) is added dropwise at room temperature via a dropping funnel in the course of an hour. A colorless precipitate was gradually formed in the course of the dropwise addition. The reaction solution was warmed to room temperature overnight and then the resultant precipitate was filtered off. The reaction solution was washed twice with 100 mL of water each time and dried over MgSO$_4$. Then, the solvent was removed in a rotary evaporator and the crude product was distilled in vacuo. Boiling point 43-44° C./7.7-8.4 10$^{-1}$ mbar. This gave 50.7 g (71%) of the pure product as a colorless clear liquid, storage at 7° C., stabilized with 4-methoxyphenol.

$^1$H NMR (CDCl$_3$): δ=1.21 (s, 6H, CH$_3$), 2.30 (br s, 1H, OH), 3.99 (s, 2H, CH$_2$), 5.81 (dd, $^3J_{H,H}$=10.5 Hz, 1.5 Hz, 1H) 6.12 (dd, $^3J_{H,H}$=10.5 Hz, 1.7 Hz, 1H), 6.39 ppm (dd, $^3J_{H,H}$=1.5 Hz, 17 Hz, 1H).

$^{13}$C NMR (CDCl$_3$): δ=26.05 (2C, CH$_3$), 69.72 (1C, COH), 72.01 (1C, CH$_2$), 127.99 (1C, HC=CH$_2$), 131.19 (1C, HC=CH$_2$), 166.08 ppm (1C, ROC=O).

Example 2: [(Chlorodimethylsilyl)oxy)]-2-methylpropyl Acrylate (Formula III, R$^2$=R$^3$=R$^4$=Me, R$^5$=CH$_2$, R$^6$=H, b=2, c=1)

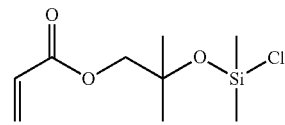

22.4 g (0.17 mol) of dichlorodimethylsilane were initially charged in the flask under argon. 5.00 g (35 mmol) of 2-hydroxy-2-methylpropyl acrylate, 4.05 g of triethylamine (40 mmol) and 10 ml of dry methyl tert-butyl ether were mixed under argon and added dropwise to dichloromethylsilane in the course of an hour under ice cooling. Following a reaction time of 2 hours, the ice bath was removed and the reaction continued at room temperature overnight. After the reaction had ended, the crude product was distilled to obtain 5.8 g (71%) of a clear colorless liquid of boiling point 41-44° C./0.41 mbar. Stabilization by admixture of 4-methoxyphenol and storage at 4° C. in the fridge.

$^1$H NMR (CDCl$_3$): δ=0.296 (s, 6H, (CH$_3$)$_2$SiCl), 1.21 (s, 6H, CH$_3$), 3.89 (s, CH$_2$), 5.69 (dd, J$_{H,H}$=10.5 Hz, 1.5 Hz, 1H), 6.00 (dd, J$_{H,H}$=10.5 Hz, 17.5 Hz, 1H), 6.28 ppm (dd, J$_{H,H}$=1.5 Hz, 17.5 Hz, 1H).

$^{13}$C NMR (CDCl$_3$): δ=4.57 (2C, Si(CH$_3$)$_2$C$_1$), 26.79 (2C, CH$_3$), 71.53 (1C, CH$_2$), 75.21 (1C, C(CH$_3$)$_2$), 128.28 (1C, H C=CH$_2$), 130.97 (1C, HC=CH$_2$), 165.84 ppm (1C, RO C=O).

$^{29}$Si-NMR (CDCl$_3$) δ=4.88 ppm ((CH$_3$)$_2$SiCl).

Example 3: Acrylate-Functional Polysiloxane

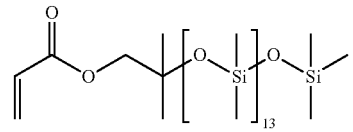

138 g (0.141 mol) of a terminally hydroxyl-functionalized polysiloxane (MW 980, chain length n=13) were diluted with 150 ml of methyl tert-butyl ether and admixed with 17.1 g (0.169 mmol) of triethylamine. Under argon and under agitation 40.0 g (0.169 mol) of [(chlorodimethylsilyl)oxy)]-2-methylpropyl acrylate (formula III, R$^2$=R$^3$=R$^4$=Me, R$^5$=CH$_2$, R$^6$=H, b=2, c=1) were admixed and the mixture was stirred at room temperature for 72 hours under exclusion of light. The ammonium salt formed as a solid material was filtered off. The organic phase was concentrated and then devolatilized in a short path evaporator at 70° C./4.2·10$^{-2}$ mbar.

Yield 134 g (85.1%).

$^1$H NMR (CDCl$_3$): δ=0.025-0.150 (m, 72H, Si(CH$_3$)$_2$), 1.29 (s, 6H, CH$_3$), 3.99 (s, 2H, CH$_2$), 5.81 (dd, $J_{H,H}$=10 Hz, 1.5 Hz, 1H), 6.13 (dd, $J_{H,H}$=10 Hz, 17 Hz, 1H), 6.41 ppm (dd, $J_{H,H}$=1.5 Hz, 17.5 Hz, 1H).

$^{13}$C NMR (CDCl$_3$): δ=1.04-1.13 (m, Si(CH$_3$)$_2$), 1.70-1.81 (m, Si(CH$_3$)$_2$), 26.97 (2C, CH$_3$), 72.16 (1C, CH$_2$), 72.91 (1C, CH$_2$C(CH$_3$)$_2$), 128.53 (1C, HC═CH$_2$), 130.64 (1C, HC═CH$_2$), 165.99 ppm (1C, ROC═O).

$^{29}$Si NMR (CDCl$_3$): δ=-22.07--21.93 (11 Si, (CH$_3$)Si), -21.39 (1Si, (CH$_3$)$_3$SiOSi(CH$_3$)$_2$), -18.71 (1 Si, (CH$_3$)$_2$COSi(CH$_3$)$_2$O), 7.25 ppm (1 Si, (CH$_3$)$_3$Si).

Example 4: Stability of Acrylate-Functional Polysiloxane from Example 3 in Water 0.7 ml of the acrylate-functional polysiloxane from Example 3 was stirred with 0.9 ml of water at room temperature for altogether 8 days and the two phases were separately analyzed by NMR spectroscopy. No detectable hydrolytic scissioning reaction had taken place.

Example 5: Acrylate not in Accordance with the Present Invention and not Stable to Water 0.78 g of acrylate-functional polysiloxane having the formula (CH$_3$)$_3$Si—O—[Si(CH$_3$)$_2$—O]$_{11}$—Si(CH$_3$)$_2$—O—CH$_2$—CH$_2$—OCO—CH═CH$_2$ and 0.9 g of water were stirred at room temperature for 2 hours and the polymer phase was analyzed by $^1$H NMR spectroscopy under admixture of trichloroacetyl isocyanate as derivatization reagent for Si—OH groups. The formation of 20 mol % of Si—OH chain ends was detected.

What is claimed is:

1. A composition comprising a (meth)acrylate-functional organosilicon compound M in which an oxygen atom connects a (meth)acrylate group to a silicon of the organosilicon compound, wherein the carbon atom bonded to the oxygen atom bears at least one further moiety bonded via carbon, with the proviso that in the presence of just one further moiety, said moiety contains more than one carbon atom, comprising at least one unit of formula I and at least one unit of formula II $$R^2{}_b X_c SiO_{[4-(b+c)]/2} \quad (I),$$

$$R^1{}_a SiO_{(4-a)/2} \quad (II),$$

where
R$^1$ and R$^2$ are each independently hydrogen or C$_1$-C$_{20}$ hydrocarbon or C$_1$-C$_{15}$ hydrocarbonoxy moieties in which one or more nonadjacent methylene units are optionally replaced by —O—, —CO—, —COO—, —OCO— or —OCOO or NR$^x$ groups, and which are unsubstituted, or substituted with a substituent —CN, NR$^x{}_2$, COOH, COOR$^x$, -halogen, -acryloyl, -methacryloyl, -epoxy, —OH, or —CONR$^x{}_2$,
R$^x$ is hydrogen or a C$_1$-C$_{10}$ hydrocarbon moiety unsubstituted or substituted with a substituent —CN or halogen,
X is an oxygen-bonded moiety of formula (III)

$$O—C(R^3R^4)—R^5—O—(C═O)—CR^6═CH_2) \quad (III)$$

R$^3$ and R$^4$ are each independently hydrogen or C$_1$-C$_{20}$ hydrocarbon moieties in which one or more nonadjacent methylene units are optionally replaced by O—(C═O)—CR$^6$═CH$_2$, —O—, —CO—, —COO—, —OCO— or —OCOO— or NR$^x$ groups, with the proviso that when R$^3$ is hydrogen, R$^4$ contains at least two carbon atoms, R$^5$ is a divalent C$_1$-C$_{20}$ hydrocarbon moiety in which one or more nonadjacent methylene units are optionally replaced by —O—, —CO—, —COO—, —OCO— or —OCOO— or NR$^x$ groups,
R$^6$ is hydrogen or unbranched, branched or cyclic saturated or unsaturated alkyl of 1 to 12 carbon atoms or aryl or aralkyl, wherein nonadjacent methylene units may be replaced by nitrogen atoms or oxygen atoms,
a is 0, 1, 2 or 3,
b is 0, 1 or 2,
c is 1, 2 or 3, and
b+c is 1, 2 or 3.

2. The (meth)acrylate-functional organosilicon compound M of claim 1, wherein R$^1$ and R$^2$ are each straight-chain, branched or cyclic C$_1$-C$_6$ alkyl or alkoxy moieties, or phenyl or vinyl moieties.

3. The (meth)acrylate-functional organosilicon compound M of claim 2, wherein R$^3$ and R$^4$ are each independently selected from methyl, ethyl and (meth)acryloyloxymethyl.

4. The (meth)acrylate-functional organosilicon compound M of claim 3, wherein R$^5$ is a divalent C-bonded C$_1$-C$_6$ hydrocarbon moiety wherein nonadjacent methylene groups are optionally replaced by oxygen.

5. The (meth)acrylate-functional organosilicon compound M of claim 2, wherein R$^5$ is a divalent C-bonded C$_1$-C$_6$ hydrocarbon moiety wherein nonadjacent methylene groups are optionally replaced by oxygen.

6. The (meth)acrylate-functional organosilicon compound M of claim 1, wherein R$^3$ and R$^4$ are each independently selected from methyl, ethyl and (meth)acryloyloxymethyl.

7. The (meth)acrylate-functional organosilicon compound M of claim 6, wherein R$^5$ is a divalent C-bonded C$_1$-C$_6$ hydrocarbon moiety wherein nonadjacent methylene groups are optionally replaced by oxygen.

8. The (meth)acrylate-functional organosilicon compound M of claim 1, wherein R$^5$ is a divalent C-bonded C$_1$-C$_6$ hydrocarbon moiety wherein nonadjacent methylene groups are optionally replaced by oxygen.

9. A process for preparing a (meth)acrylate-functionalized organosilicon compounds M of claim 1, constructed of at least one unit of formula I and no or at least one unit of general formula II $$R^2{}_b X_c SiO_{[4-(b+c)]/2} \quad (I),$$

$$R^1{}_a SiO_{(4-a)/2} \quad (II),$$

comprising:
reacting a (meth)acryloyl-functionalized chlorosilane of formula IV $$R^2{}_b X_c SiCl_{[4-(b+c)]} \quad (IV)$$

with a hydroxyl-functionalized organosilicon compounds.

10. A process for preparing a (meth)acrylate-functionalized chlorosilanes of formula IV of claim 9, $$R^2{}_b X_c SiCl_{[4-(b+c)]} \quad (IV),$$

comprising:
reacting a (meth)acryloyl-functionalized alcohol of formula V $$HO—C(R^3R^4)—R^5—O—(C═O)—CR^6═CH_2 \quad (V)$$

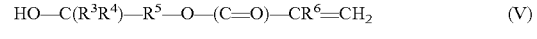

with a chlorosilane of formula VI $$R^2{}_b SiCl_{[4-b]} \quad (VI).$$

11. A (meth)acryloyl-functionalized chlorosilane of formula IV $$R^2{}_b X_c SiCl_{[4-(b+c)]} \quad (IV).$$

* * * * *